United States Patent
Johnson, III

(10) Patent No.: US 7,658,720 B2
(45) Date of Patent: Feb. 9, 2010

(54) ORTHOPEDIC APPLIANCE WITH MOISTURE MANAGEMENT SYSTEM

(75) Inventor: G. W. Jim Johnson, III, Boca Raton, FL (US)

(73) Assignee: DJO, LLC, Vista, CA (US)

( * ) Notice: Subject to any disclaimer, the term of this patent is extended or adjusted under 35 U.S.C. 154(b) by 617 days.

(21) Appl. No.: 10/726,343

(22) Filed: Dec. 2, 2003

(65) Prior Publication Data

US 2004/0167447 A1    Aug. 26, 2004

Related U.S. Application Data

(60) Provisional application No. 60/430,414, filed on Dec. 3, 2002.

(51) Int. Cl.
*A61F 5/00* (2006.01)
(52) U.S. Cl. .................. 602/14; 602/1; 36/3 R
(58) Field of Classification Search .......... 36/140, 36/3 R, 147; 602/5, 13, 16, 20, 23, 27, 60–62, 602/65, 1, 3, 14, 17–30, 41–79
See application file for complete search history.

(56) References Cited

U.S. PATENT DOCUMENTS

| | | | |
|---|---|---|---|
| 3,955,565 A | 5/1976 | Johnson, Jr. | |
| 4,280,489 A | 7/1981 | Johnson, Jr. | |
| 4,628,945 A | 12/1986 | Johnson, Jr. | |
| 5,489,259 A * | 2/1996 | Jacobs et al. | 602/13 |
| 6,041,519 A * | 3/2000 | Cheng | 36/3 R |
| 6,134,720 A | 10/2000 | Foreman | |
| 6,269,485 B1 | 8/2001 | Foreman | |
| 6,406,450 B1 | 6/2002 | Kowalczyk et al. | |
| 6,547,751 B1 | 4/2003 | Barberio | |
| 2002/0178621 A1 * | 12/2002 | Darby | 36/140 |

* cited by examiner

*Primary Examiner*—Glenn Richman
(74) *Attorney, Agent, or Firm*—Ropes & Gray LLP

(57) ABSTRACT

An orthopedic appliance such as a body brace or a prosthesis includes a substantially rigid structure adapted to be placed against a body portion. The orthopedic appliance of the invention includes a moisture management system for facilitating the removal of moisture that would otherwise accumulate between the affected body portion and the substantially rigid structure. The moisture management system includes a plurality of ventilation holes through the substantially rigid structure, and means for facilitating the transfer of moisture directly out through the ventilation holes to the atmosphere. The facilitating means can include a flexible support means disposed between the substantially rigid body portion, the support means either being porous, or the support means having a plurality of holes therethrough in alignment with the holes in the substantially rigid structure. The orthopedic device may also include a fabric liner disposed against the body portion, the fabric liner serving to wick away moisture directly through the vent holes, and also serving to provide sufficient compression to prevent window edema.

20 Claims, 2 Drawing Sheets

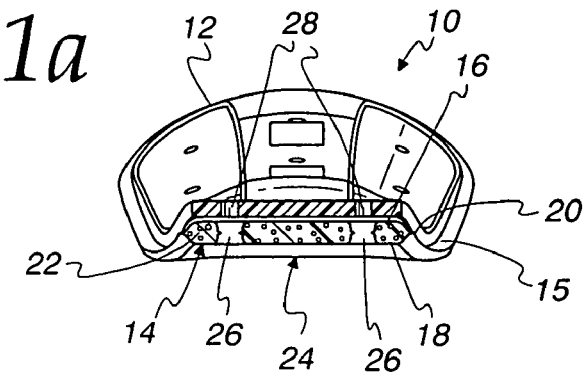
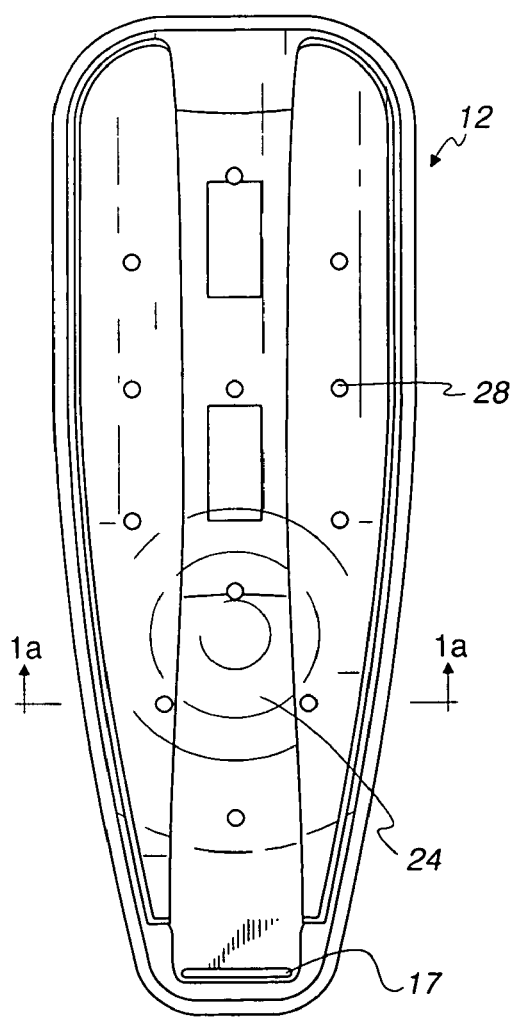
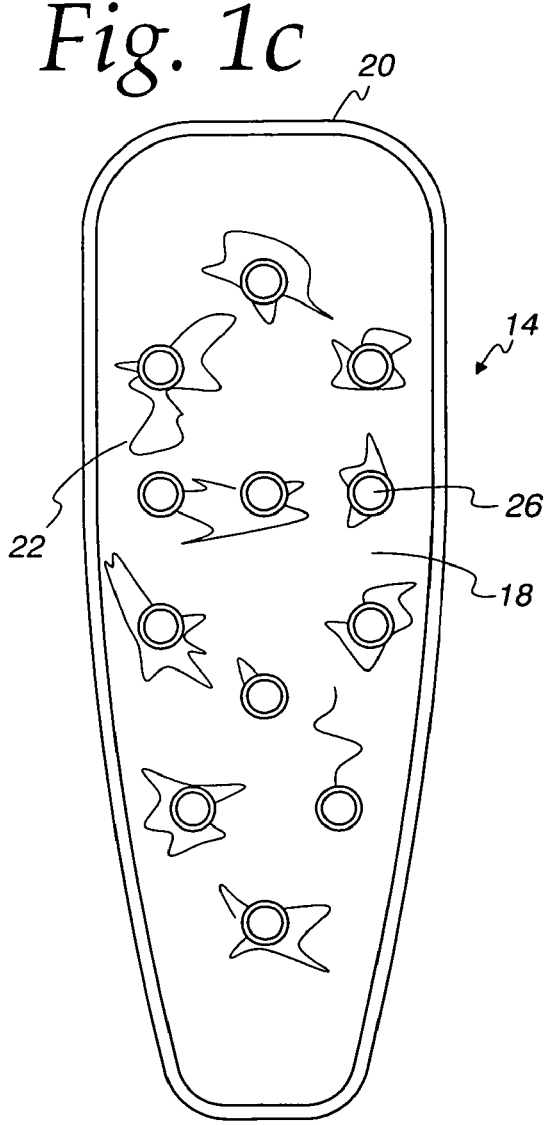

ORTHOPEDIC APPLIANCE WITH MOISTURE MANAGEMENT SYSTEM

This application claims the benefit under 35 U.S.C. § 119 (e) of provisional application Serial No. 60/430,414, filed Dec. 3, 2002, entitled "Brace with Moisture Management System."

BACKGROUND OF THE INVENTION (1) Field of the Invention

The present invention relates in general to orthopedic appliances, and, in particular, to orthopedic appliances having improved moisture management.

(2) Description of Related Art

Orthopedic appliances such as orthoses and prostheses are well known in the art. Prostheses include replacements for missing or amputated limbs. Orthoses include body braces used in the treatment of injured body parts, such as, for example, ankle braces and walking braces. For instance, the intent of an ankle brace is to provide support for an injured ankle while the ankle is healing and to stabilize the ankle against inversion and eversion without restricting plantoflexion and dorsiflexion.

Such ankle braces have utilized a pair of substantially rigid shell members, usually of a stiff, durable, molded plastic material generally shaped to conform to the lateral and medial sides of the lower extremity, respectively. In some cases, a base member, having a pair of hinge portions with distal ends, is formed from a common piece of flexible woven nylon material that has bonded thereon a layer of fastener material such as hook and loop material. The distal ends of the hinge portions are inserted in slots proximal to the lower ends of the shell members and are fastened to an area of mating hook and loop material attached to the inside surfaces of the shell members.

In order to protect the ankle from direct contact with the substantially rigid shell members, it is well known to provide a flexible support member between the ankle and the shell members. See U.S. Pat. Nos. 4,628,945 and 4,280,489, assigned to the assignee herein and incorporated herein by reference in their entireties.

As set forth in commonly assigned U.S. Pat. No. 6,406,450, also assigned to the common assignee and incorporated herein by reference in its entirety, the recovery rate for ankle function following an inversion sprain may be related to the effectiveness of edema control at the injury site. Numerous authors have reported the use of a U-shaped felt or foam rubber device beneath an elastic wrap or adhesive tape for applying focal compression to the soft tissues adjacent to the fibular malleolus. Focal compression involves pressure application to surface concavities of a body part while adjacent proximal convex bony prominences are left uncompressed.

U.S. Pat. No. 3,955,565 discloses an orthopedic apparatus comprising two nesting half shell members that surround a limb. The half-shell members are each provided with columns of apertures hat serve to reduce the weight of the apparatus, to allow longitudinal flexing of the apparatus, and to allow ventilation to the atmosphere. Each shell is provided with one or more air cells, which can include an outer covering or sleeve of absorptive material. These sleeves of absorptive material serve to transfer or wick away moisture that accumulates between the user's skin and the inner surface of the air cell that contacts the user, by directing the moisture from the front of the air cell around the edge of the air cell to the back of the air cell, and then out through the apertures.

In ankle braces, in order to ventilate the affected portion of the ankle, holes have been formed in the rigid outer shell members. Such holes can allow heat that accumulates beneath the shell to vent to the atmosphere, but may not be sufficient to remove moisture that accumulates beneath the shell. Such accumulated moisture can result in unacceptable skin irritation for the user. Another potential problem with such vent holes is that the affected portion of the ankle can be forced outwardly in the areas of the holes, in what is known as "window edema." This, of course, is an undesirable condition that should not exist in the control and treatment of any body injuries, including ankle injuries.

Thus, it is one object of the invention to provide orthopedic appliances, including orthoses and prostheses, that facilitate the removal of moisture that would otherwise accumulate between the body brace and a user's skin, and preferably that do not promote "window edema" in the user.

SUMMARY OF THE INVENTION

The present invention solves the problems of the prior art by providing an orthopedic appliance in the form of a prosthesis or a body brace, such as an ankle brace, with a moisture control system. In a preferred embodiment, the orthopedic appliance also does not promote unwanted "window edema" effects that can occur.

The orthopedic appliance herein will be described in relation to an ankle brace. However, it should be understood that the invention can be used with other appliances such as arm braces, leg braces, prostheses, and the like, in which a substantially rigid surface of the appliance is in operative engagement with a portion of a user's body. The invention, when in the form of an ankle brace, comprises substantially rigid outer shell members that are to be conformed to each side of an injured ankle, with ventilation holes formed in the substantially rigid plastic members to allow air to circulate. In one embodiment, a flexible support member is in the form of a full contact liner of porous material affixed to the inside of each shell member that faces the ankle. The porous material can be either a piece of porous foam or a porous spacer fabric, or a porous foam used with a porous spacer fabric. The porous material allows body moisture to pass directly through the porous material liner to the holes in the substantially rigid shell members and from there to the atmosphere, while at the same time providing compression on the user's ankle to avoid "window edema."

In another embodiment, the flexible support member comprises an air cell, the air cell may contain a porous material to provide for pre-inflation thereof, the air cell having circumferentially sealed vent holes therethrough, the holes through the air cell being aligned with the holes in the substantially rigid shell members. The holes in the air cell allow moisture to escape from the skin of the affected ankle portion through the aligned holes in the substantially rigid shell members to the atmosphere. In a preferred embodiment, a moisture wicking material is affixed to the surface of the air cell that is in contact with the user to facilitate the transfer of moisture from the user's skin, through the vent holes in the air cell and the shell, and out to the atmosphere. In the preferred embodiment, this moisture wicking material can also provide compression to the ankle portion sufficient to avoid "window edema."

Thus, the invention relates to an improved body brace that provides ventilation of the affected area by allowing moisture to escape to the atmosphere while at the same time providing sufficient compression to the affected portion of the body without the occurrence of "window edema."

The invention also relates to an improved body brace wherein a flexible support member is placed between the affected portion of the ankle and the substantially rigid outer shell members, the flexible support member also containing ventilation "openings" that communicate with holes in the substantially rigid outer shell members to enable adequate moisture control. In a preferred embodiment, the flexible support member also applies sufficient compression to the affected ankle portion to avoid "window edema."

Further, the invention relates to an improved body brace having a moisture wicking material for promoting the transfer of moisture from the skin of the affected body portion through ventilation holes in the body brace and out to the atmosphere.

In one embodiment, the moisture wicking material is associated directly with the inside of the substantially rigid outer shell support members for direct contact with both the ankle portion and the holes in the substantially rigid outer shell members.

In another embodiment, the moisture absorbing material is sealingly attached at its periphery to the periphery of a flexible support member that can be in the form of an air cell, a porous spacer fabric, or a porous foam. An air cell flexible support member will contain a plurality of ventilation holes aligned with the ventilation holes in the substantially rigid outer shell support members.

Thus, an embodiment of the invention relates to an orthopedic appliance, including prostheses and orthoses, having a moisture control system, the orthopedic appliance comprising at least one substantially rigid outer support member having ventilation holes therein, and moisture transferring material associated with the side of the orthopedic appliance facing the body, said moisture transferring material transferring moisture from the skin of the affected body portion to the ventilation holes in the substantially rigid outer support member while simultaneously providing sufficient compression to prevent "window edema" from occurring.

BRIEF DESCRIPTION OF THE DRAWINGS

These and other objects of the present invention will be more fully disclosed when taken in conjunction with the following detailed description of the drawings in which like numbers represent like elements and wherein:

FIG. 1a is a cross-sectional view of a first embodiment of an orthopedic appliance of the instant invention;

FIG. 1b is a plan view of the shell of the orthopedic appliance of FIG. 1a;

FIG. 1c is a plan view of the flexible support member of the orthopedic appliance of FIG. 1a;

DETAILED DESCRIPTION OF THE DRAWINGS

Figure 2:
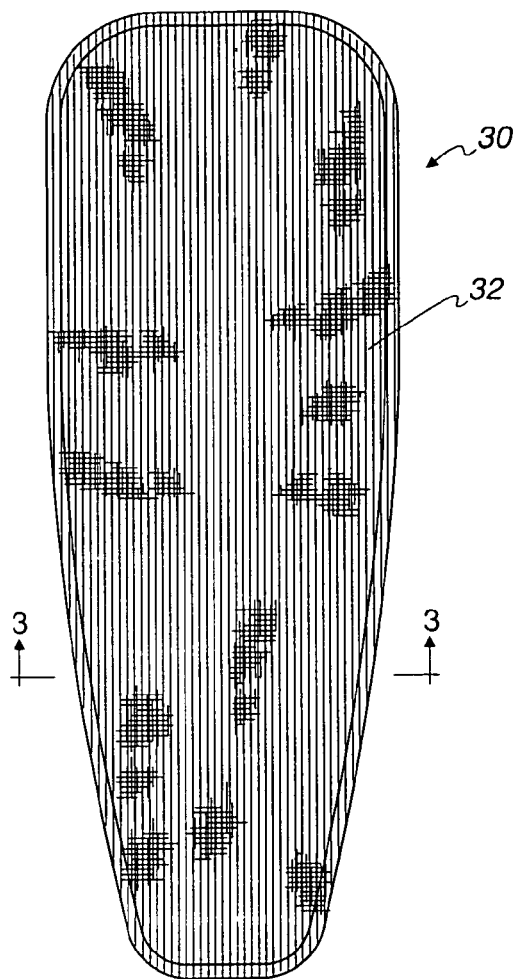
FIG. 2 is a plan view of the interior facing side of a second embodiment of the present invention wherein a moisture transferring or wicking member is attached at its outer edges to a flexible support member that is affixed to the interior facing side of a rigid ankle support member having ventilation holes therein.

As stated previously, the invention herein will be described in relation to an ankle support brace. However, it is to be understood that the invention may also be used in conjunction with any orthopedic appliance in which a substantially rigid surface is in operative engagement with a body part of a user, including body braces such as arm braces, leg braces, and the like and prostheses. The invention lies in the proper bracing of an affected body portion, along with means for facilitating the removal of moisture that might otherwise accumulate between the orthopedic appliance and the skin of the affected body portion. In a preferred body orthopedic appliance of the invention, a flexible support member is disposed between the substantially rigid surface of the orthopedic appliance and the body portion, and a wicking material is disposed between the flexible support member and the body portion to transfer moisture from the body portion to the atmosphere. In a particularly preferred embodiment, the construction of the inventive orthopedic appliance can prevent "window edema."

For purposes of illustration, FIG. 1a is a cross-sectional view of one half of an ankle brace support such as is generally shown and described in U.S. Pat. No. 4,280,489, but adapted to incorporate the structure of the present invention. The brace 10 comprises a substantially rigid shell member 12, which is preferably injection molded from a suitable thermoplastic material such as polypropylene. The shell member 12, illustrated in plan view in FIG. 1b, is contoured to the typical anatomical shape of the lower extremity and may include a pronounced indentation 24 for comfortably fitting and receiving the malleoli. Secured to each shell 12, as by a suitable adhesive, is a flexible support member 14 as illustrated in plan view in FIG. 1c. In the illustrated embodiment, flexible support member 14 is an air cell comprising two layers 16 and 18 of air-impermeable plastic such as PVC or urethane heat sealed around their edges 20 and enclosing an open-cell foam material 22. Thus, the air cell 14 is constructed to be pre-inflated and designed to afford a comfort layer between the lower extremity and the substantially rigid shell 12. Both the shells 12 and the air cells 14 can be configured to provide a relatively large proximal indentation 24 to accommodate the malleoli. A slot 17 in each shell 12 provides a means for each shell 12 to be attached to a U-shaped stirrup portion, not shown, which fits underneath the foot of the wearer. Thus, it can be seen that the ankle brace shell assembly 10 provides rigid support such that the ankle is stabilized against eversion and inversion without restricting plantoflexion and dorsiflexion. Further, the air cell assembly 14 provides some measure of comfort to the patient wearing the brace.

As a component of this invention, holes 28 are provided at various pre-selected locations throughout the area of the shells 12. The holes 28 can be round or elongated; the size, shape, number, and distribution of the holes 28 will depend on the size of the shell 12, the body part with which the shell is intended to be used, and the need to preserve the structural integrity of the shell 12. Generally the sizes of the holes 28 will range from about a few square millimeters up to about a few square centimeters. Further in accordance with the invention, air cell 14 is provided with holes 26 generally of the same size, shape, number, and distribution as the holes 28 in shell 12, such that holes 26 in the air cells 14 are positioned in alignment with the holes 28 in the shells 12. Holes 26 can be formed by locally sealing together layers 16 and 18 of air cell 14 in certain pre-selected areas to form "dimples" in the air cell, and then cutting or punching a hole through the locally sealed area or "dimple", the cut hole being slightly smaller than the locally sealed area such that the circumference of the hole is defined by the remaining portion of the locally sealed area. In this manner, the air cell 14 remains air-impermeable and still provides proper support and comfort to the user. Corresponding holes can be provided in the open-cell foam material 22 either before it is assembled into the air cell 14, or during the step of locally sealing the layers 16 and 18. Moisture and perspiration that would otherwise accumulate between layer 18 of air cell 14 and the skin of the affected body part can evaporate away directly through the holes 26 in air cell 14 and holes 28 in shell 12. Thus, the structure of FIG. 1 embodying the present invention provides improved ventilation and moisture control for the user as compared to the prior art.

While in the illustrated embodiment the flexible support member 14 is shown as an air cell, the invention is not so limited. The flexible support member could be a cell filled with an appropriate fluid or a gel, or it could be a solid gel material or a non-porous foam pad in an appropriate covering. Holes in such a flexible support member could be provided as discussed above in connection with an air cell. Alternatively, flexible support member 14 could be a porous open cell foam pad, or other porous material, with or without a porous fabric cover on one or both sides. If the foam pad itself and/or the fabric covering are non-porous, then holes can be provided therethrough in alignment with the holes in the shell member as illustrated in the embodiment of FIGS. 1a-1c. If both the foam pad and the optional fabric covering are porous, it may be possible to eliminate the holes in the flexible support member, if the porosity is sufficient to allow air and moisture to flow from the user's skin through the porous foam and fabric and out through the holes in the shell member.

It will be appreciated that in some cases, the embodiment of FIG. 1 may allow "window edema" to occur because the aligned holes in the air cell are in contact with the flesh of the ankle. Whether or not window edema will occur may depend on the size of the holes 26 and 28, the pressure with which the brace 10 is applied, and the medical condition of the user generally and of the body part in particular. The occurrence of window edema is an undesirable condition; conversely, control of edema hastens the healing of the affected body part.

Figure 3:
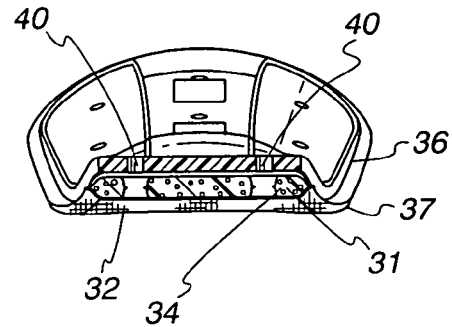
FIG. 3 is a cross-sectional view taken along the line 3-3 of FIG. 2.

An embodiment of the present invention that addresses this concern is shown in plan view in FIG. 2 and in cross-section view in FIG. 3. Brace 30 comprises a substantially rigid shell member 36 having a plurality of ventilation holes 40 formed therein, similar to the structure illustrated in FIG. 1b. A flexible support member 34 is attached to the inner surface of shell 36 by adhesive or other suitable means. The flexible support means 34 can be a non-porous structure such as an air cell, with or without a foam insert; or a cell filled with another fluid or gel, or a solid gel material, or a non-porous foam. In each of these embodiments, the flexible support member 34 will be provided with holes as shown substantially in FIG. 1c. Alternatively, the flexible support member 34 can be a porous foam material, with or without a porous fabric cover, in which case the holes are optional. In a further aspect of the invention, an inner liner 32 comprises a moisture absorbing/transferring/wicking material that is in contact with the flesh portion of the ankle. Liner 32 not only provides comfort, but also transfers moisture from the skin of the affected ankle portion to the atmosphere through the flexible support member 34 and out through the holes 40 in the substantially rigid shell 36. Liner 32 can be joined to flexible support member 34 such as by sealing the two together around their peripheries 37, as shown in FIG. 2. The combination of the liner 32 and the flexible support member 34 may then be permanently or removably attached to the substantially rigid outer support shell 36. Advantageously, liner 32 is a moisture wicking material that provides sufficient surface compression to avoid "window edema."

Figure 4:
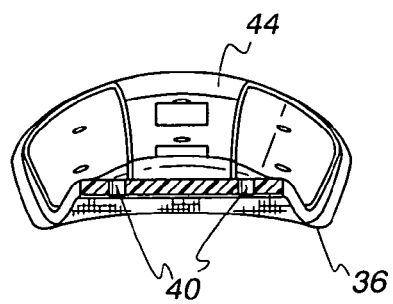
FIG. 4 is a cross-sectional view of a third embodiment of the present invention wherein a moisture transferring or wicking member is attached directly to the interior facing side of a substantially rigid ankle support member having ventilation holes therein.

FIG. 4 is a cross-section view of a third embodiment of the present invention. A substantially rigid shell member 36 is provided with a plurality of holes, such as generally illustrated in FIG. 1b. A liner of material 44 is, again, a moisture absorbing/transferring/wicking material that engages the flesh portion of the affected ankle and, in combination with the outer support shell 36 provides sufficient compression to avoid "window edema." In addition, the moisture transferred or wicked by the moisture absorbing liner material 44 is passed through the holes 40 in the substantially rigid outer shell 36 to the atmosphere. Here, again, the moisture is transferred from the patient to the atmosphere while providing comfort to the patient and while providing sufficient compression to the flesh to prevent it from attempting to be forced through the orifices in the substantially rigid outer shell 36 as "window edema."

Thus there has been disclosed several embodiments of a novel orthopedic appliance with a moisture management system that provides proper support to an injured body portion while allowing moisture to be dissipated to the atmosphere, and preferably providing sufficient uniform compression to the body portion to prevent "window edema" from occurring. While the concept of the invention has been illustrated for an embodiment in which the orthopedic appliance is an orthosis, and in particular an ankle brace, it will be understood that the concept of the invention is applicable to other orthoses such as leg braces, walking braces, arm braces, and the like, as well as to prosthetic devices. The concept of the invention is applicable to any appliance in which a substantially rigid surface is used adjacent a body part, and the substantially rigid surface is capable of having a plurality of ventilation holes formed therethrough. It also will be apparent to those skilled in the art of orthopedic devices that certain equivalents can be substituted for certain of the elements and materials specifically disclosed herein. For example, other equivalent materials might be used for the flexible support member. All such equivalents are intended to be encompassed by the claims appended hereto.

What is claimed is:

1. An orthopedic appliance for application to a body portion, said orthopedic appliance comprising
    a substantially rigid structure, said substantially rigid structure having an inner surface and an outer surface, said substantially rigid structure having a plurality of holes therethrough at pre-selected locations;
    a flexible support member comprising a top layer and a bottom layer; and
    a liner affixed to the flexible support member and adapted to be positioned next to the body portion, said liner being of a material that facilitates the transfer of moisture from the body portion out through said holes of said substantially rigid structure to the atmosphere, and wherein the flexible support member is positioned between the substantially rigid structure and the liner.

2. The orthopedic appliance of claim 1 wherein said liner provides substantially uniform compression to the body part to prevent the occurrence of window edema.

3. The orthopedic appliance of claim 1, wherein the orthopedic appliance includes a prosthesis.

4. The orthopedic appliance of claim 1, wherein the orthopedic appliance includes an orthosis.

5. The orthopedic appliance of claim 4 wherein said orthosis is selected from the group consisting of an ankle brace, a leg brace, a walking brace, and an arm brace.

6. The orthopedic appliance of claim 1 wherein said flexible support member is provided with a plurality of holes therethrough.

7. The orthopedic appliance of claim 1 wherein said flexible support member is selected from the group consisting of an air cell, a cell filled with a gel, a cell filled with a fluid, a solid gel material, a non-porous foam pad, and a porous foam pad.

8. The orthopedic appliance of claim 7 wherein said flexible support member is an air cell and said air cell contains a foam material.

9. The orthopedic appliance of claim 1 wherein said flexible support material is a porous material.

10. The orthopedic appliance of claim 9 wherein said porous material is an open-cell foam.

11. The orthopedic appliance of claim 6, wherein the plurality of holes located in the flexible support member include a sealed interface between the top layer and the bottom layer of the flexible support member.

12. The orthopedic appliance of claim 6, wherein the liner covers at least one of the holes located in the flexible support member.

13. The orthopedic appliance of claim 6, wherein the liner covers at least one of the holes located in the substantially rigid structure.

14. The orthopedic appliance of claim 1, wherein the flexible support member is pre-inflated.

15. The orthopedic appliance of claim 1, wherein the top layer and the bottom layer of the flexible support member are sealable around their edges.

16. The orthopedic appliance of claim 1, wherein the flexible support member is reversibly attachable to the substantially rigid structure.

17. The orthopedic appliance of claim 1, wherein the liner is sealingly attached at its periphery to the periphery of the flexible support member.

18. The orthopedic appliance of claim 6, wherein a plurality of holes in the flexible support member are in alignment with a plurality of holes in the substantially rigid structure.

19. The orthopedic appliance of claim 6, wherein at least one of the plurality of holes in the substantially rigid structure has a smaller diameter than at least one of the plurality of holes in the flexible support member.

20. The orthopedic appliance of claim 1, wherein the at least substantially rigid structure includes a pronounced indentation for receiving the malleoli of a user.

* * * * *